(12) United States Patent
Matoba

(10) Patent No.: US 8,000,439 B2
(45) Date of Patent: Aug. 16, 2011

(54) X-RAY ANALYZER AND X-RAY ANALYSIS METHOD

(75) Inventor: Yoshiki Matoba, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 102 days.

(21) Appl. No.: 12/544,572

(22) Filed: Aug. 20, 2009

(65) Prior Publication Data
US 2010/0046701 A1  Feb. 25, 2010

(30) Foreign Application Priority Data

Aug. 22, 2008  (JP) ................................. 2008-214716

(51) Int. Cl.
*G01N 23/223* (2006.01)
*G01N 23/203* (2006.01)

(52) U.S. Cl. ................ 378/46; 378/44; 378/45; 378/88; 378/90

(58) Field of Classification Search .................... 378/44, 378/45, 46, 48, 49, 50, 88, 89, 90
See application file for complete search history.

(56) References Cited

U.S. PATENT DOCUMENTS

| | | | | |
|---|---|---|---|---|
| 5,062,127 A | * | 10/1991 | Sayama et al. | 378/45 |
| 5,457,725 A | * | 10/1995 | Sato | 378/44 |
| 6,038,280 A | * | 3/2000 | Rossiger et al. | 378/50 |
| 6,295,333 B1 | * | 9/2001 | Tamura | 378/44 |
| 6,345,086 B1 | * | 2/2002 | Ferrandino et al. | 378/44 |
| 6,359,962 B1 | * | 3/2002 | Yagi | 378/44 |
| 6,404,846 B1 | * | 6/2002 | Hasegawa et al. | 378/44 |
| 6,522,718 B2 | * | 2/2003 | Sato | 378/50 |
| 6,798,863 B2 | * | 9/2004 | Sato | 378/46 |
| 6,810,106 B2 | * | 10/2004 | Sato | 378/50 |
| 6,855,930 B2 | * | 2/2005 | Okuda et al. | 250/310 |
| 6,885,726 B2 | * | 4/2005 | Uehara et al. | 378/44 |
| 6,965,663 B2 | * | 11/2005 | Ohzawa | 378/44 |
| 7,245,696 B2 | * | 7/2007 | Yun et al. | 378/45 |

FOREIGN PATENT DOCUMENTS

JP  2007-292476 A  11/2007

* cited by examiner

*Primary Examiner* — Allen C. Ho
(74) *Attorney, Agent, or Firm* — Brinks Hofer Gilson & Lione

(57) ABSTRACT

An X-ray tube which irradiates a primary X-ray to an irradiation point on a sample, an X-ray detector which detects a characteristic X-ray and a scattered X-ray emitted from the sample and outputs a signal including energy information of the characteristic X-ray and scattered X-ray, an analyzer which analyzes the signal, a first observation system which optically observes a surface of the sample in order to determine the irradiation point, and a second observation system which has a smaller depth of field than the first observation system, optically observes a narrow region, and measures the distance from the determined irradiation point by focus adjustment are included.

5 Claims, 1 Drawing Sheet

X-RAY ANALYZER AND X-RAY ANALYSIS METHOD

RELATED APPLICATIONS

This application claims priority under 35 U.S.C. §119 to Japanese Patent Application No. JP2008-214716 filed on Aug. 22, 2008, the entire content of which is hereby incorporated by reference.

BACKGROUND OF THE INVENTION

1. Field of the Invention

The present invention relates to an X-ray analyzer and an X-ray analysis method for performing fluorescent X-ray analysis and the like of a sample surface.

2. Description of the Related Art

In fluorescent X-ray analysis, an X-ray emitted from an X-ray source is irradiated onto a sample, a fluorescent X-ray which is a characteristic X-ray emitted from the sample is detected by an X-ray detector, and a spectrum is acquired from the energy and a qualitative analysis or quantitative analysis of the sample is performed. Fluorescent X-ray analysis is widely used in process management, quality management, and the like since a sample is quickly analyzed without being broken. In recent years, as measurement of small amounts becomes possible due to improvements in precision and sensitivity, fluorescent X-ray analysis is expected to be widely used particularly as an analysis method of detecting harmful substances included in a material, a composite electronic component, and the like.

In the related art, for example, in JP-A-2007-292476 (Claims, FIG. 1), a composite apparatus having a revolver which enables free switching between an objective lens of an optical microscope and an X-ray generator of an X-ray analyzer on the same optical axis is suggested. In the composite apparatus, it is not necessary to move a sample to an analysis position detected by the optical microscope and then align the position to be analyzed according to the movement, as the X-ray analysis can be performed by irradiating a primary X-ray from the X-ray generator under conditions in which the same sample position is maintained. Moreover, in the composite apparatus, the sample is observed while changing the magnification of the objective lens by the revolver, and alignment in the z direction is set beforehand such that the focal position of the objective lens and the focal position of the primary X-ray match each other.

The following problems remain in the known technique described above.

In the known X-ray analyzer, the sample is observed using the optical microscope in order to specify and designate a measurement point first. However, when performing quantitative analysis and the like, it is necessary to measure the distance between the specified measurement position (irradiation point) and the X-ray optical system, such as the X-ray source, with high precision. In the technique disclosed in JP-A-2007-292476, a configuration measuring the distance up to the measurement position is not adopted since the focal position of the objective lens and the focal position of the primary X-ray are set beforehand to match each other. Furthermore, in this technique, an optical system, such as a mirror, is used to dispose the optical microscope and the X-ray optical system on the same axis, but an optical microscope with a large field of view is preferable for specifying the measurement position. In this case, an optical system, such as a large mirror, is needed. However, since a large space for the mirror is required in this case, the distance between the X-ray source and the sample is increased. As a result, it is difficult to obtain high sensitivity.

Furthermore, an example of a method of measuring the distance between the measurement position and the X-ray optical system, such as the X-ray source, by the optical microscope includes a method of measuring the distance by the focal distance of the optical microscope. In the case of this method, particularly when designating a measurement position for an uneven sample, high operability is obtained as the depth of field increases. However, when measuring the distance from the measurement position, a small depth of field is preferable in order to measure the distance with high precision. For this reason, when performing distance measurement using an optical microscope which specifies the measurement position, there is a problem that the precision of the distance measurement is low because the depth of field was large.

SUMMARY OF THE INVENTION

In view of the above, it is an object of the invention to provide an X-ray analyzer and an X-ray analysis method which are excellent in operability when specifying a measurement position and which are capable of measuring distance with high precision.

The invention adopts the following configuration in order to solve the above-described problems. That is, according to an aspect of the invention, an X-ray analyzer includes: a radiation source which irradiates a radial ray to an irradiation point on a sample; an X-ray detector which detects a characteristic X-ray and a scattered X-ray emitted from the sample and outputs a signal including energy information on the characteristic X-ray and scattered X-ray; an analyzer which analyzes the signal; a first observation system which optically observes a surface of the sample in order to determine the irradiation point; and a second observation system which has a smaller depth of field than the first observation system, optically observes a narrow region, and measures the distance from the determined irradiation point by focus adjustment.

In addition, according to another aspect of the invention, an X-ray analysis method of irradiating a radial ray from a radiation source to an irradiation point on a sample, detecting a characteristic X-ray and a scattered X-ray emitted from the sample and outputting a signal including energy information of the characteristic X-ray and scattered X-ray by an X-ray detector, and analyzing the signal by an analyzer includes: optically observing a surface of the sample using a first observation system in order to determine the irradiation point; and measuring the distance from the determined irradiation point by focus adjustment using a second observation system which has a smaller depth of field than the first observation system and which optically observes a narrow region.

Thus, in the X-ray analyzer and the X-ray analysis method, the surface of the sample is optically observed by the first observation system in order to determine the irradiation point, and the distance from the irradiation point is measured by focus adjustment using the second observation system which has a smaller depth of field than the first observation system and which can optically observe a narrow region. Accordingly, the high operability can be obtained by specifying the irradiation point with the first observation system which can observe a wide region and has a large depth of field, and the distance from the sample can be measured with high precision by the second observation system which can observe a narrow region and has a small depth of field.

Moreover, in the X-ray analyzer according to the aspect of the invention, it is preferable to further include a processing unit that calculates the distance between the radiation source and the irradiation point on the basis of the distance from the irradiation point measured by the second observation system and corrects the result analyzed by the analyzer according to the distance.

Moreover, in the X-ray analysis method according to the aspect of the invention, it is preferable to further include calculating the distance between the radiation source and the irradiation point on the basis of the distance from the irradiation point measured by the second observation system and correcting the result analyzed by the analyzer according to the distance using a processing unit.

That is, in the X-ray analyzer and the X-ray analysis method, the processing unit calculates the distance between the radiation source and the irradiation point on the basis of the distance from the irradiation point measured by the second observation system and corrects the result analyzed by the analyzer according to the distance. Accordingly, highly precise quantitative analysis and the like become possible by performing the correction on the quantitative calculation and the like.

Moreover, in the X-ray analyzer according to the aspect of the invention, it is preferable to further include: a sample stage on which the sample is placed; and a moving mechanism which moves the sample stage between an observation region based on the first observation system and an observation region based on the second observation system. The first and second observation systems may be disposed at different positions, and an optical component of the second observation system may be movably provided on an optical axis of a radial ray emitted from the radiation source. That is, in the X-ray analyzer, since the optical component of the second observation system is movably provided on the optical axis of the radial ray emitted from the radiation source, the second observation system is an optical system with a narrow field of view and a small optical component which can be disposed even in a small space may be used as an adopted optical component, such as a mirror. Accordingly, it becomes possible to bring the radiation source and the sample close to each other, compared with the case where the optical element of the first observation system is disposed on the optical axis. As a result, better sensitivity can be obtained.

According to the invention, the following effects are obtained.

That is, in the X-ray analyzer and the X-ray analysis method according to the aspects of the invention, the surface of the sample is optically observed by the first observation system in order to determine the irradiation point, and the distance from the irradiation point is measured by focus adjustment using the second observation system which has a smaller depth of field than the first observation system and which can optically observe a narrow region. Accordingly, high operability can be obtained by specifying the irradiation point with the first observation system which can observe a wide region and has a large depth of field, and the distance from the sample can be measured with high precision by the second observation system which can observe a narrow region and has a small depth of field.

BRIEF DESCRIPTION OF THE DRAWINGS

FIGURE is a view schematically illustrating the entire configuration of an X-ray analyzer in an embodiment of the X-ray analyzer and X-ray analysis method according to the invention.

DETAILED DESCRIPTION OF THE PREFERRED EMBODIMENTS

Figure 1:
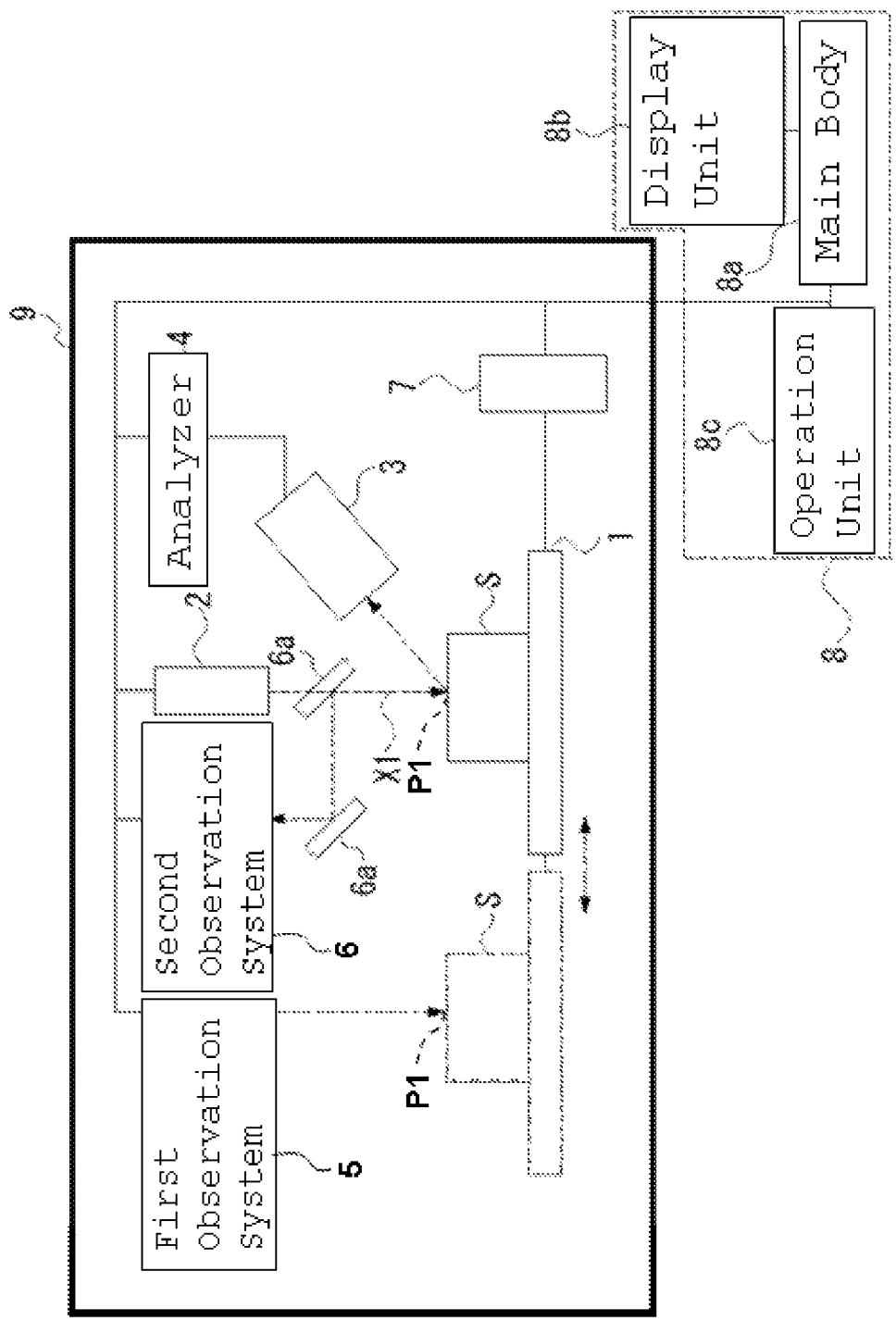

Hereinafter, an embodiment of the X-ray analyzer and X-ray analysis method according to the invention will be described with reference to FIGURE.

The X-ray analyzer of the present embodiment is an energy dispersive fluorescent X-ray analyzer, for example. As shown in FIGURE, the X-ray analyzer of the present embodiment includes: a sample stage 1 on which a sample S is placed and which is movable; an X-ray tube (radiation source) 2 which irradiates a primary X-ray (radial ray) X1 to an arbitrary irradiation point P1 on the sample S; an X-ray detector 3 which detects a characteristic X-ray and a scattered X-ray emitted from the sample S and outputs a signal including the energy information of the characteristic X-ray and scattered X-ray; an analyzer 4 which is connected to the X-ray detector 3 and analyzes the above signal; a first observation system 5 which can optically observe a surface of the sample S in order to determine the irradiation point P1; a second observation system 6 which has a smaller depth of field than the first observation system 5 and which can optically observe a narrow region and can measure the distance from the determined irradiation point P1 by focus adjustment; a moving mechanism 7 which can move the sample stage 1 between an observation region based on the first observation system 5 and an observation region based on the second observation system 6; and a processing unit 8 which is connected to the analyzer 4 and performs analysis processing to determine the X-ray intensity corresponding to a specific element.

The X-ray tube 2 emits an X-ray, which is generated when a thermal electron generated from a filament (cathode) in the tube is accelerated by a voltage applied between the filament (cathode) and a target (anode) and collides with the W (tungsten), Mo (molybdenum), Cr (chromium), and the like of the target, as the primary X-ray X1 through a window, such as a beryllium foil.

The X-ray detector 3 includes a semiconductor detection element (not shown; for example, an Si (silicon) element which is a pin-structure diode) provided at an X-ray incidence window. When one X-ray photon is incident, the X-ray detector 3 generates a current pulse corresponding to the one X-ray photon. The instantaneous current value of the current pulse is proportional to the energy of the incident characteristic X-ray. In addition, the X-ray detector 3 is set to convert the current pulse generated in the semiconductor detection element into a voltage pulse and amplify and output the voltage pulse as a signal.

The analyzer 4 is a pulse height analyzer (multi-channel pulse height analyzer) which obtains the pulse height of a voltage pulse from the signal and generates an energy spectrum.

The first observation system 5 is an optical microscope which is disposed at a different position from the second observation system 6, has an observation region at a different position from an observation region of the second observation system 6, and is configured to include a camera for observation by which an enlarged image and the like of the sample S disposed in the observation region can be viewed and imaged.

The second observation system 6 is an optical microscope configured to include an optical microscope, a camera for observation, and the like by which an enlarged image and the like of the sample S can be viewed and imaged through a plurality of mirrors 6a provided. In addition, at least the mirror 6a disposed on the optical axis of the primary X-ray X1 is of a movable type, in order that the mirror 6a can move back from the optical axis of the primary X-ray X1 at the time of analysis.

The sample stage 1 is an XYZ stage which can move vertically and horizontally and whose height can be adjusted in a state where the sample S is fixed thereon.

In addition, the moving mechanism 7 is configured to include a stepping motor which is connected to the sample stage 1 or is provided in the sample stage 1 in order to move the sample stage 1 vertically and horizontally. The moving mechanism 7 makes the sample stage 1 movable between the observation region based on the first observation system 5 and the observation region based on the second observation system 6.

The processing unit 8 is a computer which is configured to include a CPU and the like and functions as an analysis processing device. The processing unit 8 includes: a main body 8a of a control unit which determines the X-ray intensity corresponding to a specific element from the energy spectrum transmitted from the analyzer 4; a display unit 8b which displays the analysis result on the basis of the X-ray intensity; and an operation unit 8c which can input various commands for positioning the irradiation point P1, analysis conditions, and the like.

The processing unit 8 has a function of calculating a distance between the X-ray tube 2 and the irradiation point P1 on the basis of the distance from the irradiation point P1 measured by the second observation system 6 and a function of correcting the result analyzed by the analyzer 4 according to the distance.

The sample stage 1, the X-ray tube 2, the X-ray detector 3, the first observation system 5, the second observation system 6, and the like are housed in a sample chamber 9 which can be decompressed. At the time of measurement, the sample chamber 9 is decompressed so that the X-ray is not absorbed into the air.

Next, an X-ray analysis method using the X-ray analyzer of the present embodiment will be described with reference to FIGURE.

First, the sample S is set on the sample stage 1 and then the sample chamber 9 is set to have a predetermined decompressed state. The processing unit 8 drives the sample stage 1 using the moving mechanism 7 so that the sample S is moved and disposed in the observation region of the first observation system 5. Then, by observing the surface of the sample S over a wide range using the first observation system 5 and arbitrarily determining and designating the irradiation point P1, the XY coordinates of the designated irradiation point P1 are recorded. In this case, the plurality of irradiation points P1 may be designated to perform multipoint analysis.

Then, the processing unit 8 drives the sample stage 1 using the moving mechanism 7 so that the sample S is moved and disposed in the observation region of the second observation system 6. Then, the surface of the sample S is observed over a narrow range using the second observation system 6, the distance corresponding to best focusing is measured using image processing while changing the focal position at the irradiation point P1 of the XY coordinates, and the distance from the irradiation point P1 to the X-ray tube 2 is calculated from the information. In addition, in the case where the plurality of irradiation points P1 has been designated, the distance is measured and calculated for each irradiation point P1.

Then, a characteristic X-ray and a scattered X-ray generated by moving the mirror 6a on the optical axis of the primary X-ray X1 backward and irradiating the primary X-ray X1 from the X-ray tube 2 onto the sample S are detected by the X-ray detector 3.

Then, the X-ray detector 3 which detected the X-rays transmits the signal to the analyzer 4, and the analyzer 4 acquires an energy spectrum from the signal and outputs it to the processing unit 8.

The processing unit 8 determines the X-ray intensity corresponding to a specific element from the energy spectrum transmitted from the analyzer 4 and displays the analysis result on the display unit 8b.

In this case, the processing unit 8 corrects the result (the concentration or film thickness of the element to be analyzed) analyzed by the analyzer 4 according to the calculated distance between the X-ray tube 2 and the irradiation point P1 and performs accurate quantitative determination.

Thus, in the X-ray analyzer and the X-ray analysis method of the present embodiment, the surface of the sample S is optically observed by the first observation system 5 in order to determine the irradiation point P1, and the distance from the irradiation point P1 is measured by focus adjustment using the second observation system 6 which has a smaller depth of field than the first observation system 5 and which can optically observe a narrow region. Accordingly, high operability can be obtained by specifying the irradiation point P1 with the first observation system 5 which can observe a wide region and has a large depth of field, and the distance from the sample can be measured with high precision by the second observation system 6 which can observe a narrow region and has a small depth of field.

In addition, the processing unit 8 calculates the distance between the X-ray tube 2 and the irradiation point P1 on the basis of the distance from the irradiation point P1 measured by the second observation system 6 and corrects the result analyzed by the analyzer according to the distance. Accordingly, highly precise quantitative analysis and the like become possible as a result of performing this correction for quantitative calculation or the like.

In addition, since the mirror 6a which is an optical component of the second observation system 6 is movably provided on the optical axis of the primary X-ray X1 emitted from the X-ray tube 2, the second observation system 6 is an optical system with a narrow field of view and a small mirror which can be disposed even in a small space may be used as the adopted mirror 6a. Accordingly, it becomes possible to bring the X-ray tube 2 and the sample S close to each other, compared with the case where an optical component of the first observation system 5 is disposed on the optical axis. As a result, better sensitivity can be obtained.

It should be understood that the technical scope of the invention is not limited to the above embodiment, but various modifications may be made without departing from the spirit and scope of the invention.

For example, although the analysis is performed in a condition where the sample chamber is decompressed in the above-described embodiment, the analysis may also be performed in a condition where the sample chamber is not in a vacuum (decompressed) state.

In addition, although the invention is applied to the energy dispersive fluorescent X-ray analyzer in the above-described embodiment, the invention may also be applied to X-ray analyzers using other analysis methods, for example, a wavelength dispersive fluorescent X-ray analyzer and an SEM-EDS (scanning electron microscope and energy dispersive X-ray analysis) apparatus which uses an electron ray as an irradiated radial ray and which can also obtain a secondary electron image.

What is claimed is:

1. An X-ray analyzer comprising:
   a radiation source which irradiates a radial ray to an irradiation point on a sample;
   an X-ray detector which detects a characteristic X-ray and a scattered X-ray emitted from the sample and outputs a signal including energy information on the characteristic X-ray and scattered X-ray;
   an analyzer which analyzes the signal;
   a first observation system which optically observes a surface of the sample in order to determine the irradiation point; and
   a second observation system which has a smaller depth of field than the first observation system, optically observes a narrow region, and measures a distance from the determined irradiation point by focus adjustment.

2. The X-ray analyzer according to claim 1, further comprising:
   a processing unit that calculates a distance between the radiation source and the irradiation point on the basis of the distance from the irradiation point measured by the second observation system and corrects a result analyzed by the analyzer according to the distance between the radiation source and the irradiation point.

3. The X-ray analyzer according to claim 1, further comprising:
   a sample stage on which the sample is placed; and
   a moving mechanism which moves the sample stage between an observation region based on the first observation system and an observation region based on the second observation system,
   wherein the first and second observation systems are disposed at different positions, and
   an optical component of the second observation system is movably provided on an optical axis of a radial ray emitted from the radiation source.

4. An X-ray analysis method of irradiating a radial ray from a radiation source to an irradiation point on a sample, detecting a characteristic X-ray and a scattered X-ray emitted from the sample and outputting a signal including energy information of the characteristic X-ray and scattered X-ray by an X-ray detector, and analyzing the signal by an analyzer, the method comprising:
   optically observing a surface of the sample using a first observation system in order to determine the irradiation point; and
   measuring a distance from the determined irradiation point by focus adjustment using a second observation system which has a smaller depth of field than the first observation system and which optically observes a narrow region.

5. The X-ray analysis method according to claim 4, further comprising:
   calculating a distance between the radiation source and the irradiation point on the basis of the distance from the irradiation point measured by the second observation system and correcting a result analyzed by the analyzer according to the distance between the radiation source and the irradiation point using a processing unit.

* * * * *